United States Patent [19]

Baekkeskov et al.

[11] Patent Number: 5,674,692
[45] Date of Patent: Oct. 7, 1997

[54] METHODS FOR DIABETES SUSCEPTIBILITY ASSESSMENT IN ASYMPTOMATIC PATIENTS

[76] Inventors: Steinunn Baekkeskov, 285 Beacon St., San Francisco, Calif. 94131; Henk-Jan Aanstoot, 1428 10th Ave., No. 3, San Francisco, Calif. 94122

[21] Appl. No.: 346,313

[22] Filed: Oct. 28, 1994

Related U.S. Application Data

[63] Continuation of Ser. No. 48,886, Apr. 16, 1993, abandoned, which is a continuation-in-part of Ser. No. 984,935, Dec. 3, 1992, abandoned, which is a continuation-in-part of Ser. No. 756,207, Sep. 6, 1991, abandoned.

[51] Int. Cl.$^6$ ...................... G01N 33/564; G01N 33/567
[52] U.S. Cl. .......................... 435/7.21; 435/7.4; 436/506; 436/518
[58] Field of Search ........................ 435/7.21, 7.4, 435/973; 436/506, 518, 536, 811

[56] References Cited

FOREIGN PATENT DOCUMENTS

WO91/17186  11/1991  WIPO.

OTHER PUBLICATIONS

Pak et al., Human Pancreatic Islet Cell Specific 38 Kilodalton Autoantigen identified by Cytomegalovirus–Induced Monoclonal Islet Cell Autoantibody, Diabetologia 33(9):569–572, 1990.

Rabin et al., Cloning and Expression of IDDM–Specific Human Autoantigen Diabetes 41:183–186, 1992.

Baekkeskov et al., Autoantibodies in Newly Diagnosed Diabetic Children Immunopreciptate Human Pancreatic Islet Cell Proteins. Nature 298: 167–169, 1982.

Aanstoot et al. "Humoral and cellular response to a 38kD islet cell autoantigen in type–1 diabetes," *Diabetes 40* Supp. 1 Abstract 898, p. 225A (1991).

Baekkeskov et al. "Identification of the 64K autoantigen in insulin–dependent diabetes as the GABA–synthesizing enzyme glutamic acid decarboxylase," *Nature* 347:151–156 (1990).

Christie et al., "Distinct antibody specificities to a 64–kD islet cell antigen in type 1 diabetes as revealed by trypsin treatment," *J. Exp. Med.*, 172:789–794 (1990).

Christie et al., "Antibodies to GAD and tryptic fragments of islet 64K antigen distinct markers for development of IDDM. Studies with identical Twins." *Diabetes*, 41:782–878 (1992).

Ko et al. "Studies on autoimmunity for initiation of Beta–cell destruction VIII. Pancreatic Beta–cell dependent autoantibody to a 38 kilodalton protein precedes the clinical onset of diabetes in BB rats," *Diabetologia* 34:548–554 (1991).

Roep et al. "T–cell clones from a type–1 diabetes patient respond to insulin secretory granule proteins," *Nature* 345:632–634 (1990).

Roep et al. "T–cell reactivity to 38 kD insulin–secretory–granule protein in patients with recent–onset type 1 diabetes," *Lancet* 337:1439–1441 (1991).

Seißler et al., "Antibodies to the $M_r$ 64,000 (64K) protein in islet cell antibody positive non–diabetic individuals indicate high risk impaired Beta–cell function," *Diabetologia* 35:550–554 (1992).

Arden et al., Imogen 38: A Novel 38–kD Islet Mitochondrial Autoantigen Recognized by T Cells from a Newly Diagnosed Type 1 Diabetic Patient, J. Clin. Invest. 97:551–561, 1996.

I.Y. Ko et al., Studies on autoimmunity for initiation of Beta–cell destruction VIII. Pancreatic Beta–cell dependent autoantibody to a 38 kilodalton protein precedes the clinical onset of diabetes in BB rats, Diabetologia 34:548–554, 1991.

S. Baekkeskov et al., Antibodies to an Mr 64,000 Human Islet Cell Protein in the Prediabetic Period of IDDM Patients, Ann. N.Y. Acad. Sci. 475:415–417, 1986.

*Primary Examiner*—Marian C. Knode
*Assistant Examiner*—Donna C. Wortman
*Attorney, Agent, or Firm*—Townsend & Townsend & Crew

[57] ABSTRACT

Assays for identifying human patients at risk for developing insulin-dependent diabetes mellitus rely on detection of autoantibodies to a 38 kD autoantigen present in pancreatic β-cells in patient sera. It has been found that autoantibodies to this particular autoantigen developed in patients well before clinical onset of the disease in a significant subpopulation of prediabetic patients. Useful assays will frequently combine detection of autoantibodies to the 38 kD autoantigen with detection of other known markers of IDDM, such as autoantibodies to a 64 kD autoantigen (glutamic acid decarboxylase).

10 Claims, 3 Drawing Sheets

METHODS FOR DIABETES SUSCEPTIBILITY ASSESSMENT IN ASYMPTOMATIC PATIENTS

This application is a continuation of Ser. No. 08/048,886, filed on Apr. 16, 1993, now abandoned, which is a continuation-in-part of Ser. No. 07/984,935, filed on Dec. 3, 1992, now abandoned, which is a continuation-in-part of Ser. No. 07/756,207, filed on Sep. 6, 1991, now abandoned, the full disclosures of which are incorporated herein by reference.

This invention was made with government support under Grant No. DK 41822-01-04 awarded by the National Institutes of Health. The Government has certain rights in this invention.

BACKGROUND OF THE INVENTION

1. Field of the Invention

The present invention relates generally to methods for identifying patients who are at risk of developing insulin-dependent diabetes mellitus (IDDM). More particularly, the present invention relates to the detection of an approximately 38 kD autoantigen associated with diabetes in serum of patients prior to clinical onset of the disease.

Insulin-dependent diabetes mellitus (IDDM) primarily afflicts young people. Although insulin is available for treatment, the several-fold increased morbidity and mortality associated with this disease urge the development of early diagnostic and preventive methods. The destruction of pancreatic β-cells, which precedes the clinical onset of IDDM, is mediated by autoimmune mechanisms. Among the most thoroughly studied autoimmune abnormalities associated with the disease is the high incidence of circulating β-cell specific autoantibodies at the time of diagnosis. Family studies have shown that the autoantibodies to certain β-cell autoantigens appear prior to overt IDDM by a number of years, suggesting a long prodromal period of humoral autoimmunity before clinical symptoms emerge. The family studies have also documented a slow, progressive loss of insulin response to intravenous glucose in the years preceding diagnosis. The presence of β-cell specific autoantibodies in the prediabetic period is likely to reflect the ongoing autoimmune process, one that eventually leads to critical β-cell depletion and insulin dependency. It has been estimated that only 10% of the total β-cell mass remains at the time of clinical onset.

Thus, methods for early and accurate identification of susceptible individuals are needed. Assays that can detect autoantibodies associated with early humoral autoimmunity accompanying β-cell destruction are particularly desirable. The classical method for detecting islet cell autoantibodies (ICA) is by immunohistology using frozen pancreatic sections. Family studies, however, have shown that the β-cell cytoplasmic antibodies measured by this method are of insufficient specificity to serve as a single marker of susceptibility. Moreover, ICA are very difficult to standardize, and interpretation of the stained section is subject to observer bias. Thus, there has been no way to define what is a "positive" specimen. More accurate assays may be achieved by employing more specific markers, either alone or in combination with ICCA. Alternative markers include autoantibodies to an approximately 64 kD autoantigen, insulin autoantibodies, and MHC class II DR/DQβ haplotype.

The 64 kD autoantigen holds particular promise as a diagnostic marker for IDDM. Autoantibodies to the 64 kD autoantigen have an incidence of from about 70% to 80%, both at the time of clinical onset of the disease and the prediabetic period. The presence of the autoantibodies has been shown to precede overt IDDM by several years and familial studies. Recently, inventors herein together with another research group have discovered that the 64 kD autoantigen of pancreatic β-cells associated with IDDM is glutamic acid decarboxylase (GAD) (E.C. 4.1.1.15) which is an abundant protein of GABA-secreting neurons in the central nervous system (CNS). Based on this discovery, numerous conventional assay formats have become available for detecting autoantibodies to the 64 kD autoantigen (GAD) to permit patient screening.

Identification of autoantibodies to the 64 kD autoantigen, however, is insufficient by itself as a screening test to identify patients at risk for developing IDDM. As stated above, autoantibodies to the 64 kD autoantigen are present in only 70% to 80% of patients who later develop IDDM, thus failing to identify a significant number of susceptible individuals. It would therefore be desirable to provide additional and alternative markers which are able to predict IDDM susceptibility in at least a portion of those patients who do not develop antibody to the 64 kD autoantigen. Such markers should be present at an early stage of β-cell destruction prior to the clinical onset of IDDM, and should remain detectable from that early stage through the time of clinical onset. This marker should be identifiable in patient serum, thus facilitating screening, and should preferably be compatible with detection of autoantibodies to the 64 kD autoantigen.

2. Description of the Background Art

Antibodies to a 38 kD antigen present in human islets have been detected by immunoprecipitation with sera from patients suffering from insulin dependent diabetes mellitus. Baekkeskov et al. (1982) Nature 298:167–169 and Aanstoot et al. (1991) Abstract 898, Diabetes 40 Supp. 1, page 225A. A 38 kD islet cell protein has been reported in the BB-rat, an animal model of insulin dependent diabetes mellitus. Ko et al. (1991) Diabetologia 34:548–554. T-cell reactivity to an insulinoma protein of approximately 38 kD has been detected in newly diagnosed diabetic patients. Roep et al. (1990) Nature 345:632–634 and Lancet (1991) 337:1439–1441.

Antibodies to the 65 kD isoform of the enzyme glutamic acid decarboxylase ($GAD_{65}$) have been identified in 70% to 80% of individuals experiencing β-cell destruction and development of insulin dependent diabetes mellitus. Baekkeskov et al. (1990) Nature 347:151–156 and WO 92/04632. Some patients having islet cell antibodies (ICA) identified by immunofluorescence of frozen pancreas sections do not have antibodies to $GAD_{65}$. Seissler et al. (1991) Diabetologia 34:548–554.

SUMMARY OF THE INVENTION

The present invention comprises methods for assessing the risk of developing insulin-dependent diabetes mellitus (IDDM) in asymptomatic human patients. The methods rely on detecting the presence of autoantibodies to a 38 kD amphiphilic membrane-bound islet cell protein having a pI in the range from 5.6 to 6.1. It has been found that autoantibodies to the 38 kD autoantigen appear in a significant subgroup of patients who later develop IDDM, with the appearance occurring well before clinical onset of the disease, usually more than one year prior to clinical onset, and often two years or more prior to clinical onset. It has been also found that autoantibodies to the 38 kD autoantigen are present in a significant number of patients who do not display autoantibodies to the 64 kD autoantigen ($GAD_{65}$). Thus, assays according to the present invention will preferably rely on detection of antibodies to both the 38 kD autoantigen and the 64 kD autoantigen ($GAD_{65}$), with the presence of either autoantibody being predictive of IDDM.

A further understanding of the nature and advantages of the invention will become apparent by reference to the remaining portions of the specification and drawings.

DESCRIPTION OF SPECIFIC EMBODIMENTS

Figure 1A:
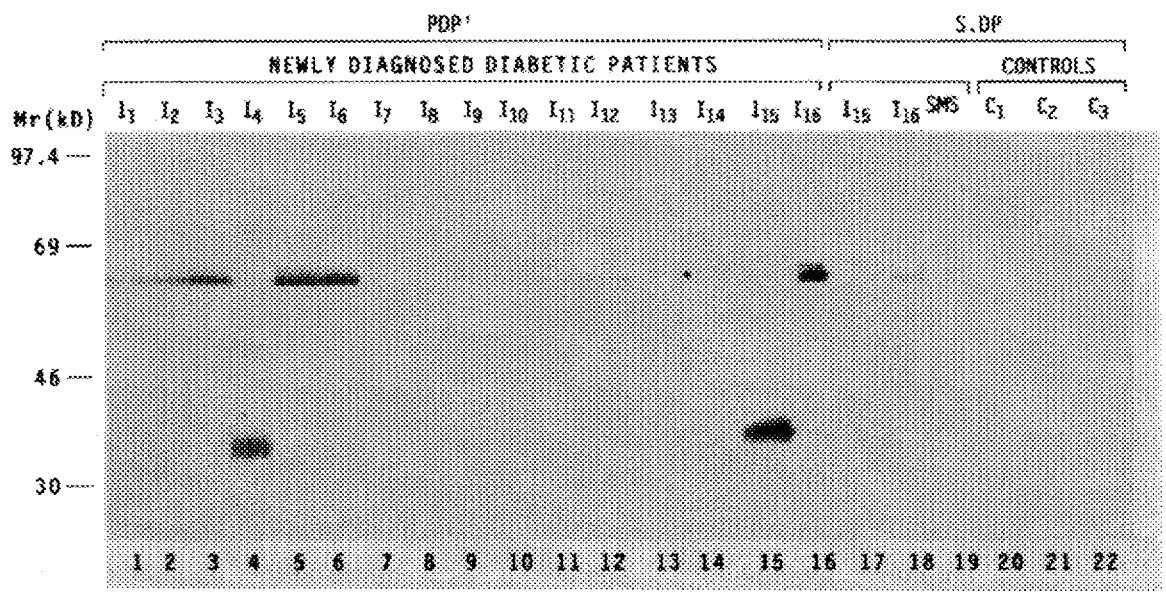
FIG. 1A is a fluorogram of an SDS-PAGE showing immunoprecipitation of membrane and cytosol fractions of $^{35}S$-methionine labeled islet cell proteins with sera from newly diagnosed diabetic patients $I_1-I_{16}$ (lanes 1–18), a stiff-man syndrome serum (lane 19) and sera from healthy controls C1–C3 (lanes 20–22). $GAD_{65}$ which splits into two bands $\alpha$ and $\beta$, can be seen in immunoprecipitates from both membrane and cytosol fractions with serum from patient $I_{16}$ (lanes 16 and 18) whereas the 38 kD protein is only detected in immunoprecipitates from the membrane fraction with serum from patient $I_{15}$ and $I_{16}$ (compare lanes 15–16 with lanes 17–18).

The present invention results from our discovery that antibodies to a particular 38 kD protein of pancreatic β-cells (which are the insulin-secreting cells of the islets of Langerhans) are released into sera of a significant subpopulation of prediabetic human patients. In particular, it has been found that such antibodies appear to be present in the sera of at least about 10% of prediabetic patients, with detectable levels of the autoantibodies appearing at the early stages of β-cell destruction, usually at least one year prior to clinical onset of insulin dependent diabetes mellitus (IDDM) and often two years or more prior to onset of the disease. Thus, the presence of autoantibodies to the 38 kD autoantigen can serve as a useful marker for identifying those otherwise asymptomatic patients who are susceptible to developing IDDM at a later time. In particular, serum autoantibodies to the 38 kD autoantigen are useful for diabetes screening when combined with detection of other serum markers, particularly autoantibodies to the 64 kD pancreatic β-cell autoantigen ($GAD_{65}$).

The 38 kD autoantigen is a membrane-bound amphiphilic protein present in the pancreatic islets or β-cells of mammalian species, such as human and rats, and is characterized by a pI in the range from about 5.4 to 6.1. The nominal molecular weight and pI range are based on comparisons with known proteins, as described in detail in the Experimental section. It will be appreciated, of course, that the molecular weight and pI range thus determined are subject to experimental error, and the present invention is not limited to these nominal characteristics of the protein. Instead, the present invention relates to the detection of autoantibodies against the autoantigen which has been isolated and identified in FIGS. 1 and 2, as described hereinafter in the Experimental section. It is the discovery that these autoantibodies are present in patient sera which is critical to the present invention, not the precise physical characteristics of the protein autoantigen.

The examples reported in the Experimental section rely on vigorous extraction of $^{35}S$-methionine labeled rat islet cell proteins in a detergent. The 38 kD autoantigen protein of the present invention is relatively insoluble in aqueous media, and it has previously been difficult to obtain suitable cell extracts for use in immunoprecipitation experiments. The particular extraction methods taught in the Experimental section, however, have provided a reliable basis for detecting presence of autoantibodies to the 38 kD autoantigen. Using the effectively solubilized islet cell proteins, it has been found that autoantibodies to the autoantigen are present in prediabetic patients with a distribution different than that found for autoantibodies to the 64 kD autoantigen ($GAD_{65}$) who are positive for islet cell antibodies (ICA) by immunofluorescence. Thus, it has been demonstrated that detection of autoantibodies to the 38 kD autoantigen in sera is a useful predictive marker for asymptomatic patients at risk of developing IDDM.

The methods of the present invention will be used to screen asymptomatic patients to determine those patients who are prediabetic, i.e. at risk of developing IDDM in the future. By "asymptomatic," it is meant that the patient is free from clinical symptoms of diabetes and has not yet suffered sufficient damage to the insulin-producing β-cells to be clinically identified as having IDDM. By "prediabetic" it is meant that the patient has developed detectable levels of circulating autoantibodies to an autoantigen on the pancreatic β-cells, such as the 38 kD autoantigen, and is at significant risk of developing IDDM in the future. The clinical onset of IDDM may be determined by conventional clinical indicia as well described in the medical literature.

A wide variety of suitable assay formats exist for detecting autoantibodies to the 38 kD autoantigen in accordance with the principles of the present invention. As described in detail in the Experimental section hereinafter, the presence of autoantibody in patient sera can be determined by immunoprecipitation with labeled 38 kD autoantigen. Labeled autoantigen can be obtained by growing suitable mammalian islet cells, such as rat or human islets, in the presence of a labeled amino acid precursor, such as $^{35}S$-methionine. The resulting labeled 38 kD antigen can then be extracted using the protocol described in the Experimental section, or other equally vigorous procedures for solubilizing the relatively insoluble autoantigen. The extracted autoantigen is then reacted with patient sera, and the resulting reaction products separated using conventional techniques, such as SDS-PAGE, or the like. Such immunoprecipitation protocols have the advantage that no purification of the 38 kD autoantigen is required and that identification of autoantibodies to the 64 kD autoantigen ($GAD_{65}$) can be performed simultaneously.

Generally, however, it will be desirable to utilize more convenient assay formats, such as immunoassays, enzyme assays, and the like. Such immunoassays and enzyme assays typically rely on exposing purified 38 kD autoantigen, or other ligand capable of binding autoantibodies to the 38 kD autoantigen, to a serum sample and detecting specific binding between the ligand and autoantibodies for the 38 kD autoantigen which may be present in the serum. Binding between the autoantibodies and the 38 kD autoantigen or equivalent ligand indicates that the autoantibodies are present in the serum sample and is diagnostic of a prediabetic condition in an asymptomatic patient prior to clinical onset of the disease.

The particular assay protocol chosen is not critical, and it is necessary only that the assay be sufficiently sensitive to detect a threshold level of the autoantibodies. Such threshold level should be as low as possible, with the only lower limit being that the assays must distinguish negative sera with no autoantibodies to the 38 kD autoantigen as present. It will be appreciated that in the very early stages of β-cell destruction, very low levels of the autoantibodies may be present. Thus, the presence of any autoantibodies above the negative background or control level will be diagnostic of the prediabetic condition.

Suitable assays include both solid phase (heterogeneous) and non-solid phase (homogeneous) protocols. The assays may be run using competitive or non-competitive formats, and using a wide variety of labels, such as radioisotopes, enzymes, fluorescers, chemiluminescers, spin labels, and the like. A majority of suitable assays rely on heterogeneous protocols where the ligand is bound to a solid phase which is utilized to separate the ligand-autoantibody complex which forms when autoantibody is present in the serum sample. A particular advantage of using a purified ligand is that it facilitates the preparation of a solid phase for use in the assay. That is, the ligand may be conveniently immobilized on a variety of solid phases, such as dipsticks, particulates, microspheres, magnetic particles, test tubes, microtiter wells, and the like.

The solid phase is exposed to the serum sample so that the autoantibody, if any, is captured by the ligand. By then removing the solid phase from the serum sample, the captured autoantibodies can be removed from unbound autoantibodies and other contaminants in the serum sample. The captured autoantibody may then be detected using the non-competitive "sandwich" technique where labeled ligand for the autoantibody is exposed to the washed solid phase. Alternatively, competitive formats rely on the prior introduction of soluble, labeled autoantibody to the serum sample so that labeled and unlabeled forms may compete for binding to the solid phase. Such assay techniques are well known and well described in both the patent and scientific literature. Exemplary immunoassays which are suitable for detecting the autoantibodies in serum include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876, the disclosures of which are incorporated herein by reference.

Particularly preferred are sensitive enzyme-linked immunosorbent assay (ELISA) methods which are described in detail in U.S. Pat. Nos. 3,791,932; 3,839,153; 3,850,752; 3,879,262; and 4,034,074. Such ELISA assays can provide measurement of very low titers of the autoantibodies.

According to the preferred ELISA technique, the purified ligand is bound either covalently or non-covalently to a solid surface. The solid surface is exposed to the serum sample where autoantibody present in the sample is captured and bound. Typically, the ligand on the solid phase will be present in excess so that the entire quantity of autoantibody may be bound. After separating the solid phase and washing its surface, the solid phase can be exposed to labeled reagent capable of specifically binding the captured autoantibody. The labeled reagent may be labeled purified ligand, or may be other ligand capable of binding to the autoantibody, e.g., labeled anti-human antibody. In this way, label is bound to the solid phase only if autoantibody was present in the serum sample. The enzyme labels may be detected by conventional visualization techniques, e.g., production of a colored dye, chemiluminescence, fluorescence, or the like.

A second preferred embodiment comprises radioimmunoassays (RIA) which are performed using a solid phase which has been prepared as described above. The solid phase is exposed to the serum sample in the presence of radiolabeled autoantibodies which can compete for binding to the immobilized ligand. In this way, the amount of radiolabel bound to the solid phase will be inversely proportional to the amount of autoantibodies initially present in the serum sample. After separation of the solid phase, non-specifically bound radiolabel can be removed by washing, and the amount of radiolabel bound to the solid phase determined. The amount of bound radiolabel, in turn, can be related to the amount of autoantibodies initially present in the sample.

Methods according to the present invention will preferably combine detection of autoantibodies to the 38 kD autoantigen with detection of other known IDDM markers, such as autoantibodies to other β-cell autoantigens, particularly autoantibodies to the 64 kD autoantigen ($GAD_{65}$) and insulin autoantibodies, and most particularly autoantibodies to the 64 kD autoantigen ($GAD_{65}$). It has been found that the presence of autoantibodies to the 38 kD autoantigen is overlapping but not coextensive with the presence of autoantibodies to the 64 kD autoantigen in prediabetic patient sera. Thus, presence of autoantibodies to either or both of the 38 kD autoantigen and the 64 kD autoantigen ($GAD_{65}$) will be diagnostic of the prediabetic condition.

Methods and compositions suitable for detecting autoantibodies to the 64 kD autoantigen ($GAD_{65}$) in patient sera are described in detail in copending applications Ser. No. 07/756,207 (which is equivalent to published PCT Application WO 92/04632) and 07/984,935, the disclosures of which are both fully incorporated herein by reference. Detection of autoantibodies to the 64 kD autoantigen (specifically the α and β forms of $GAD_{65}$) by immunoprecipitation is described in detail in the Experimental section hereinafter.

The following examples are offered by way of illustration, not by way of limitation.

Experimental

Methods

Neonatal rat islets were isolated and labeled with $^{35}S$-methionine as described in S. Baekkeskov et al., (1989) *Diabetes*, 38, 1133–1141. Islets were swollen on ice for 10 minutes in HEMAP buffer (10 mM Hepes, pH 7.4, 1 mM $MgCl_2$, 1 mM EGTA, 1 mM aminoethyl-isothiorunium bromide hydrobromide, and 0.2 mM pyridoxal phosphate), followed by homogenization by 20 strokes in a glass homogenizer. The homogenate was centrifuged at 100,000 g for 1 hour to obtain a cytosol and a particulate membrane fraction. The particular membrane fraction was extracted in HEMAP-buffer with 2% Triton X-114 for 2 hours by repeated dispersion through a bended pipette tip, followed by centrifugation at 100,000 g to remove debris. Amphiphilic proteins in both the cytosol fraction and the membrane extract were purified by temperature-induced TX-114 phase separation. See Baekkeskov et al., (1990) *Nature* 347:151–156. The detergent phase of membrane or cytosol fractions were precleared with normal human serum before immunoprecipitation with the indicated sera, as described in Baekkeskov et al. (1989), supra. Extracts of 250 rat islets (FIGS. 1A and 1B) and 500 rat islets (FIG. 2) were used per immunoprecipitate. Immunoprecipitates were analyzed by SDS-PAGE using 15% gels and processed for fluorography, as described in Baekkeskov et al. (1989), supra.

The 38 kD Protein is an Amphiphilic β-Cell Membrane Protein of pI 5.4–6.1

Figure 1B:
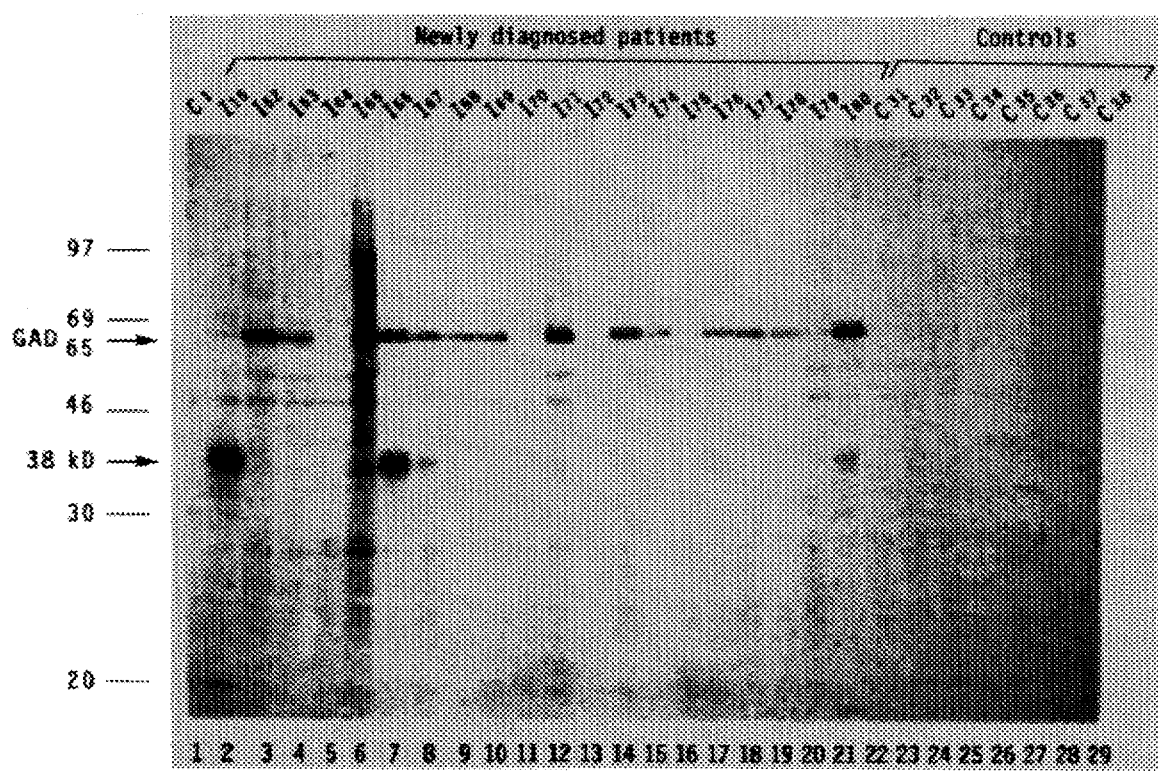
FIG. 1B depicts the immunoprecipitation of membrane fractions of $^{35}S$-methionine labeled islet cell proteins with sera from newly diagnosed diabetic patients $I_{15}$ and $I_{62}-I_{80}$ (lanes 3–21) and healthy controls $C_1$ and $C_{31}-C_{38}$. The diabetic sera recognize either the 38 kD protein alone, the $GAD_{65}$ protein alone, both proteins or no specific protein.
Figure 2:
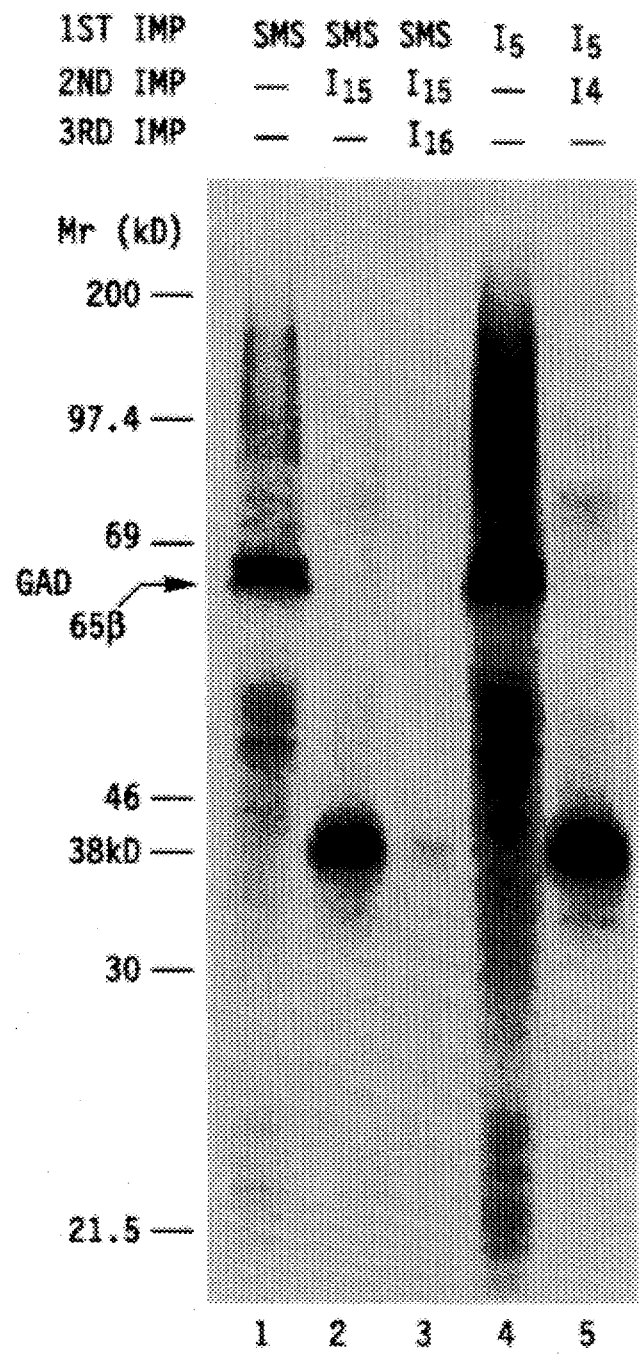
FIG. 2 is a fluorogram of an SDS-PAGE showing sequential immunoprecipitation of $^{35}S$ methionine labeled rat islets with sera positive for the anti-38 kD protein antibody and for the anti-$GAD_{65}$ antibody. Lanes 1 and 4 show immunoprecipitation with an anti-$GAD_{65}$ antibody positive stiff-man syndrome serum[4] (Lane 1), and a diabetic patient serum $I_5$ (lane 4). The supernatant after immunoprecipitation was then subjected to a second immunoprecipitation with anti-38 kD antibody positive diabetic sera $I_{15}$ and $I_4$ (lanes 2 and 5). The supernatant after immunoprecipitation in lane 2 was then subjected to a third immunoprecipitation with an anti-38 kD and anti-$GAD_{65}$ antibody positive serum $I_{16}$ (lane 3). $GAD_{65}$ and the 38 kD protein were found not to affect the immunoprecipitation of each other.

The distribution of the insoluble 38 kD protein into cytosolic and particulate islet cell fractions was analyzed, and cytosolic and membrane proteins were subjected to a Triton X-114 phase separation to assess the amphiphilicity of the 38 kD protein (FIG. 2). In contrast to the GAD autoantigen which is found as a soluble hydrophilic, a soluble amphiphilic, and a membrane bound amphiphilic form, as described in Christgau et al., (1992) *J. Cell Biol.*, 118:309–320 and Christgau et al., (1991) *J. Biol. Chem.*, 266:21257–21264, (FIG. 1A compare lanes 16 and 18), the 38 kD protein was only detected in the particulate fraction, where it partitioned into the detergent phase (FIG. 1A, lanes 15 and 16). Thus, the 38 kD protein is an amphiphilic membrane protein.

The 38 kD protein was detected as a broad band on fluorograms of SDS-gels suggesting heterogeneity in size and/or charge (FIG. 1 and 2). Two dimensional gel electrophoresis using isoelectric focusing in the first dimension and SDS-PAGE in the second dimension, as described in Baekkeskov et al. (1989) supra, revealed 7 spots of similar relative molecular weight. The corresponding pI's of 5.4–6.1 were determined by coelectrophoresis with carbamylated creatine phosphokinase charge chain markers and known HeLa cellular proteins.

In an analysis of neuroendocrine and non-endocrine cell lines, the 38 kD antigen was only detected in immunoprecipitates of βTC3 cells derived from a transgenic mouse β-cell tumor, as described in Efrat et al., *Proc. Natl. Acad. Sci.*, (1988) 85:9037–9041, whereas glucagon producing αTC cells, as described in Powers et al., (1990) *Diabetes* 39:406–414, as well as all other cell lines tested in this study were negative (Table 1). Thus expression of the 38 kD protein appears to be restricted to pancreatic β-cells.

TABLE 1

ANALYSIS OF EXPRESSION OF THE 38 kD PROTEIN IN DIFFERENT CELL LINES:

| CELL LINE | ORIGIN | EXPRESSION |
|---|---|---|
| βTC3[b] | Mouse pancreatic insulinoma | pos |
| αTC-2[c] | Mouse pancreatic glucagonoma | neg |
| PC12[a] | Rat adrenal pheochromocytoma | neg |
| CHO[a] | Chinese hamster ovary | neg |
| HeLa[a] | Human ovarian denocarcinoma | neg |
| T$_{47}$D[a] | Human ductal breast carcinoma | neg |
| Sk-NEP-1[a] | Human nephroblastoma | neg |
| Cos-1[a] | Monkey kidney tumor | neg |
| CV-1[a] | Precursor of Cos-1 | neg |
| HepG2[a] | Human hepatocellular carcinoma | neg |
| BHK-21[a] | Baby hamster kidney | neg |
| HTC[d] | Rat hepatoma | neg |

TABLE 1-continued

ANALYSIS OF EXPRESSION OF THE 38 kD PROTEIN IN DIFFERENT CELL LINES:

| CELL LINE | ORIGIN | EXPRESSION |
|---|---|---|
| TERA-2[a] | Human teratocarcinoma | neg |
| CCD-118Sk[a] | Human fibroblast | neg |

Methods: Cell lines were cultured according to established methods and labeled with $^{35}$S-methionine, Baekkeskov et al. (1989) supra. Membrane extracts were prepared and immunoprecipitated as described for neonatal rat islets in Methods, using serum I$_{1.5}$ and serum C$_1$. The immunoprecipitates were analyzed by SDS-PAGE and fluorography, Baekkesekov et al. (1989) supra.
[a]American Type Culture Collection, Bethesda, Maryland.
[b]Efrat et al. (1988) Proc. Natl. Acad. Sci. 85:9037–9041.
[c]Powers et al. (1990) Diabetes 39:406–414.
[d]Nagata and Yoon (1992) Diabetes 41:998–1008.

The 38 kD Protein is not a Fragment of GAD

Antibodies in sera from type 1 diabetic patients recognize a 37 kD trypsin fragment of GAD$_{65}$, as described in Christie et al., (1990) *J. Exp. Med.*, 172:789–794, and Christie et al., (1992) *Diabetes*, 41:782–878. Such sera do not always recognize the full length native GAD molecule, suggesting that a sequestered epitope may become exposed upon trypsinization. In light of this report, we have addressed the question whether the 38 kD protein is a fragment of GAD or otherwise related to GAD.

Islet cell membrane extracts were sequentially immunoprecipitated with sera that contained anti-GAD$_{65}$ or anti-38 kD antibodies. Supernatants depleted for immunoreactive, GAD$_{65}$ were still positive for the 38 kD protein (FIG. 2). Similarly supernatants depleted for immunoreactive 38 kD protein still contained the GAD$_{65}$ molecule. Thus, the native 38 kD protein and the native GAD$_{65}$ molecule do not display immunological crossreactivity. Next we analyzed whether anti-38 kD sera recognize a 37/40 kD fragment of GAD$_{65}$, which was generated by a mild trypsin digestion of either protein. Although several anti-GAD sera recognize the 37/40 kD GAD$_{65}$ trypsin fragment, the single anti-38 kD antibody positive sera tested were negative. Finally two 37 kD antibody positive sera did not immunoprecipitate the 38 kD antigen. These results demonstrate that the 38 kD protein is distinct from GAD.

Autoantibodies to the 38 kD Antigen are Present in a Subgroup of Prediabetic and Diabetic Individuals and Complement GAD Autoantibodies The incidence of 38 kD antibodies was analyzed and compared with prevalence of GAD antibodies and ICA in three groups. (FIG. 1 and Table 2): (i) 37 children who developed diabetes ≦5 years of age and 38 controls in the same age group, (ii) 49 individuals who developed diabetes at >5 years and 25 controls in the same age group and (iii) 44 individuals (age 2.6–49.9 years at clinical onset) whose sera had been obtained prior to clinical onset of type 1 diabetes.

The results from the three groups are shown in Table 2. In a total of 130 patients, who were analyzed either in the prediabetic period or at the clinical onset of disease, 22 (17%) were anti-38 kD antibody positive compared to 100 (77%), who were anti-GAD$_{65}$ antibody positive. Six patients were positive for anti-38 kD antibodies only, whereas 16 had both anti-38 kD and anti-GAD$_{65}$ antibodies. Thus 106 (82%) were positive for antibodies to either or both antigens. Anti-38 kD as well as anti-GAD$_{65}$ antibodies were detected at clinical onset in children who developed type 1 diabetes as early as 1.3 and 0.8 years of age respectively. Since the duration of β-cell autoimmunity in those very young children can only have been short, both proteins are likely targets of the primary rather than secondary autoimmune processes directed to the β-cell in the human disease. This circumstance is supported by the appearance of antibodies to both antigens several years before the clinical onset of type 1 diabetes. Thus the six anti-38 kD antibody positive individuals in the prediabetic group were all positive in the very first sample available (3, 9, 25, 33, 53, and 74 months before clinical onset, respectively), and antibodies persisted in follow-up samples which were available from the prediabetic period in 3/6 patients. Similarly anti-$GAD_{65}$ antibodies were detected in samples obtained 3–85 months before clinical onset, a result consistent with our earlier studies, as described in Baekkeskov et al. *J. Clin. Invest.*, 79(3), 926–934 (1987), and Atkinson et al., *Lancet*, 335:1357–1360 (1990). Thus both anti-38 kD and anti-$GAD_{65}$ antibodies can be detected in sera up to several years before clinical onset indicating that they are markers of early β-cell destruction.

diagnosed groups respectively were negative for both anti-38 kD and anti-$GAD_{65}$ antibodies, suggesting that the humoral autoimmune response in those individuals may include other target molecules at the time of clinical onset. Immunoprecipitations did not reveal islet cell protein(s) that were specifically recognized by those sera (results not shown). It is conceivable that ICA reactivity in those anti-38 kD and anti-$GAD_{65}$ antibody negative sera may be directed to non-protein molecules like gangliosides, as described in Nayak et al., (1985) *Diabetes*, 34:617–619. Finally, 8 individuals in the prediabetic group and 2 and 3 individuals in the young and older newly diagnosed groups respectively were negative for antibodies by all three assays.

The anti-38 kD antibodies analyzed in this study recognized their target under native but not denaturing conditions, suggesting that anti-38 kD antibodies, much as anti-$GAD_{65}$ antibodies, are primarily directed toward conformational epitopes. Although the destruction of β-cells is believed to be mediated primarily by T-cells rather than antibodies and

TABLE 2

INCIDENCE OF AUTOANTIBODIES TO A 38 kD βCELL MEMBRANE PROTEIN IN TYPE 1 DIABETES AND COMPARISON WITH $GAD_{65}$ab AND ICA

| GROUP | n | Avg. age at diagnosis or at sampling of sera (controls) years | Range years | F/M | ICA[a] | Incidence 38 kD auto-antibodies | Incidence $GAD_{65}$ auto-antibodies | Incidence 38 kD and/or $GAD_{65}$ auto-antibodies |
|---|---|---|---|---|---|---|---|---|
| Newly diagnosed diabetic patients <5 years of age | 37 | 2.9 ± 1.4 | 0.8–5.0 | 15/22 (68%) | 32[b]/37 (86%) | 4[e]/37 (11%) | 30/37 (81%) | 30/37 (81%) |
| Healthy controls <5 years of age | 38 | 2.8 ± 1.3 | 0.9–5.0 | 18/20 (90%) | 0/38 (0%) | 0/38 (0%) | 0/38 (0%) | 0/38 (0%) |
| Newly diagnosed diabetic patients >5 years of age | 49 | 13.1 ± 9.22 | 5.1–57.0 | 20/29 (69%) | 38[c]/49 77% | 12[f]/49 (24%) | 37/49 (76%) | 41/49 (84%) |
| Healthy controls >5 years of age | 25 | 14.9 ± 12.6 | 5.1–54.2 | 10/15 (68%) | 0/25 (0%) | 0/25 (0%) | 0/25 (0%) | 0/25 |
| Prediabetic Individuals 3-85 mos. before clinical onset | 44 | 19.2 ± 12.5 | 2.6–49.9 | 14/30 (47%) | 28[d]/44 (64%) | 6[g]/44 (14%) | 33/44 (75%) | 35/44 (80%) |

[a]ICA was analyzed by indirect immunofluorescence on frozen sections of human pancreas, as described in Greenbaum et al., (1992) Diabetes, 41:1570–1574.
[b]Four of whom were both anti-$GAD_{65}$ and anti-38 kD antibody negative.
[c]Six of whom were both anti-$GAD_{65}$ and anti-38 kD antibody negative.
[d]None of whom were anti-$GAD_{65}$ and anti-38 kD antibody negative.
[e]All of whom also had $GAD_{65}$ autoantibodies.
[f]Eight of whom also had $GAD_{65}$ autoantibodies.
[g]Four of whom also had $GAD_{65}$ autoantibodies.
n: Number of patients in Group.

The incidence of ICA detected by immunofluorescence of frozen sections of human pancreas was 75% (98/130). In the three groups, the anti-38 kD and/or anti-$GAD_{65}$ immunoprecipitation assays detected a total of 18 individuals which were negative for ICA by the immunofluorescence assay indicative of a lower sensitivity of the latter method to detect antibodies to those antigens. Blocking experiments have shown that the ICA response can progress from GAD-restricted to non-GAD restricted during the prediabetic period in some individuals which suggests a spreading of antigen reactivity during prolonged periods of β-cell destruction, as described in Atkinson et al., (1993) *J. Clin. Invest.* 91:350–356. Interestingly, all ICA positive individuals in the prediabetic group were positive for either anti-38 kD antibodies, anti-$GAD_{65}$ antibodies or both. In contrast 4 and 6 ICA positive individuals in the young and older newly complement, islet cell antibodies present during early phases of β-cell destruction seem likely to be directed toward the same antigens as the pathogenic T-cells. We have extensively analyzed immunoprecipitates of detergent lysates of $^{35}$S-methionine labeled islets with diabetic and control sera by one and two dimensional gel-electrophoresis in attempts to detect additional islet cell proteins that are specifically recognized by autoantibodies in type 1 diabetes. The stringent conditions of immunoprecipitation require that antibodies must (1) be of the IgG isotype (for binding to Protein A-Sepharose®), and (2) be of sufficient affinity and specificity to recognize their target protein in the midst of an abundance of other islet cell proteins. Using this assay, we have been unable to detect proteins other than GAD and the 38 kD protein that are consistently and specifically recognized by a significant fraction of diabetic sera. In particular, insulin, and a 69 kD protein with homology to bovine serum albumin, reported elsewhere to be targets of antibodies in diabetic sera, as described in Palmer et al., (1983) *Science*, 222:1337–1339 and Karjalainen et al., (1992) *N. Eng. J. Med.* 327:302–307, were not detected in immunoprecipitates, Baekkeskov et al. (1989), supra. Thus, strong IgG responses to protein antigens may be limited to the $GAD_{65}$ and 38 kD molecules in the human disease. Since high titer anti-$GAD_{65}$ and anti-38 kD IgG antibodies are detected in the early phases of β-cell autoimmunity, we predict the presence of activated $CD4^+$ T-helper cells recognizing each of those molecules. In fact, reactivity to both GAD and to a 38 kD β-cell protein has been demonstrated using T-cell lines from newly diagnosed diabetic patients, as described in Atkinson et al., (1992) *Lancet*, 339:458–459; Diaz et al., (1992) *Diabetes*, 41:118–121; Roep et al., (1990) *Nature*, 345:632–634; and Roep et al., (1991) *Lancet*, 337:1439–1441. The relation of the 38 kD antigen described herein with that 38 kD T-cell stimulatory protein, Roep et al., (1990) supra and Roep et al., (1991), supra, remains to be clarified.

Although the foregoing invention has been described in some detail by way of illustration and example, for purposes of clarity of understanding, it will be obvious that certain changes and modifications may be practiced within the scope of the appended claims.

What is claimed is:

1. A method for assessing the risk of developing insulin dependent diabetes mellitus (IDDM) in an asymptomatic human patient, said method comprising:

contacting autoantibodies in a serum sample from the patient with a 38 kD autoantigen, wherein the 38 kD autoantigen is an amphiphilic membrane-bound islet cell protein having a pI in the range from 5.4 to 6.1;

detecting specific binding between the 38 kD autoantigen and the autoantibodies;

wherein the specific binding indicates a likelihood of the patient developing IDDM.

2. A method as in claim 1, wherein the specific binding is detected by immunoprecipitation of the autoantibodies with labeled 38 kD autoantigen.

3. A method as in claim 1, wherein the specific binding is detected by reaction with the autoantigen immobilized on a solid phase, separation of the solid phase from the serum sample, and detection of autoantibodies bound to the solid phase.

4. The method of claim 1, wherein the 38 kD autoantigen is purified and the autoantibodies bind to a conformational epitope on the autoantigen.

5. A method for assessing the risk of developing insulin dependent diabetes mellitus (IDDM) in an asymptomatic human patient, said method comprising:

contacting autoantibodies to a 38 kD autoantigen in a serum sample from the patient with the 38 kD autoantigen, wherein the 38 kD autoantigen is an amphiphilic membrane-bound islet cell protein having a pI in the range from 5.4 to 6.1;

contacting autoantibodies to a 65 kD autoantigen in the serum sample with the 65 kD autoantigen, wherein said 65 kD autoantigen is glutamic acid decarboxylase;

detecting specific binding between the autoantibodies to the 38 kD autoantigen and the 38 kD autoantigen; and detecting specific binding between the autoantibodies to the 65 kD autoantigen and the 65 kD autoantigen;

wherein the specific binding of either or both of the autoantibodies indicates a likelihood of developing insulin dependent diabetes mellitus.

6. A method as in claim 5, wherein the specific binding of the autoantibodies to the 38 kD autoantigen is detected by immunoprecipitation with labeled 38 kD autoantigen.

7. A method as in claim 6, wherein the specific binding of the autoantibodies to the 65 kD autoantigen is detected by immunoprecipitation with labeled 65 kD autoantigen.

8. A method as in claim 5, wherein the specific binding of the autoantibodies to the 38 kD autoantigen is detected by reaction with the 38 kD autoantigen immobilized on a solid phase, separation of the solid phase from the serum sample, and detection of autoantibodies bound to the solid phase.

9. A method as in claim 8, wherein the specific binding of the autoantibodies to the 65 kD autoantigen is detected by reaction with the 65 kD autoantigen immobilized on a solid phase, separation of the solid phase from the serum sample, and detection of autoantibodies bound to the solid phase.

10. The method of claim 5, wherein the 38 kD autoantigen is purified and the autoantibodies bind to a conformational epitope on the autoantigen.

* * * * *